United States Patent [19]
Zavitsanos

[11] Patent Number: 5,135,657
[45] Date of Patent: Aug. 4, 1992

[54] CHROMATOGRAPHIC METHOD WITH MICELLAR ON-COLUMN ENRICHMENT

[75] Inventor: Apostolos P. Zavitsanos, Quebec, Canada

[73] Assignee: Hewlett-Packard Company, Palo Alto, Calif.

[21] Appl. No.: 750,153

[22] Filed: Aug. 26, 1991

Related U.S. Application Data

[63] Continuation-in-part of Ser. No. 487,332, Mar. 1, 1990, abandoned.

[51] Int. Cl.$^5$ .............................................. B01D 15/08
[52] U.S. Cl. .................................... 210/656; 210/635; 210/198.2; 436/89; 436/161; 436/178
[58] Field of Search ..................... 210/635, 656, 198.2, 210/502.1; 436/89, 161, 178; 422/70; 530/413, 417

[56] References Cited

U.S. PATENT DOCUMENTS

| | | | |
|---|---|---|---|
| 3,892,531 | 7/1975 | Gilbert | 422/70 |
| 4,548,904 | 10/1985 | Kent | 436/161 |
| 4,551,288 | 11/1985 | Kelly | 210/198.2 |
| 4,665,037 | 5/1987 | Stolowitz | 436/161 |
| 4,732,683 | 3/1988 | Georgiades | 210/635 |
| 4,743,680 | 5/1988 | Mathews | 210/656 |
| 4,797,474 | 1/1989 | Patroni | 530/351 |
| 4,828,799 | 5/1989 | Love | 436/161 |
| 4,832,849 | 5/1989 | Cardin | 210/635 |
| 4,925,567 | 5/1990 | McAleese | 210/656 |

OTHER PUBLICATIONS

Kato, "High Performance Liquid Chromatography of Membrane Proteins", Journal of Chromatography, 391 (1987), pp. 395-407.

Snyder, Introduction to Modern Liquid Chromatography, John Wiley & Sons, Inc., 1979, New York, pp. 720-731, 640, 542-549, 55, 56, 662-676, 118, 778, and 311-314.

Fitzgerald, "Admicellar Chromatography: A New Low Energy Separative Process", AICHE Symposium Series No. 250, vol. 82, 1984, pp. 142-152.

K. Slais, D. Kourilova and M. Krejci in "Trace Analysis by Peak Compression Sampling of a Large Sample Volume on Microbore Columns in Liquid Chromatography", Journal of Chromotography, 282 (1983), pp. 363-370.

P. Schauwecker et al., in "Trace Enrichment Techniques in Reversed-Phase High-Performance Liquid Chromatograpy", Journal of Chromatography, 136 (1977), pp. 63-72.

M. Krejci, K. Slais, and A. Kunath in "Comparison of Injection-Generated Gradient and Isocratic Ion-Pair Chromatography on Short Microbore Column in HPLC", Chromatographia, vol. 22, No. 7-12, Dec. 1986, pp. 311-315.

Primary Examiner—Ernest G. Therkorn

[57] ABSTRACT

On-column enrichment is provided for a sample having both polar and nonpolar analytes by mixing the sample with surfactant in a polar solvent. The surfactant causes the nonpolar analytes to be incorporated in micelles that dissolve in the polar solvent. The concentration of surfactant is maintained at a level sufficient to maintain the micelles as the mixture is introduced onto the head of a chromatographic column. Once sample introduction is completed, the mixture is diluted so that the surfactant concentration drops below that required to maintain the micelles, which thus break up. The analytes are then separated using reverse-phase gradient elution.

4 Claims, 3 Drawing Sheets

300 

```
┌─────────────────────────────────┐
│    OBTAINING SAMPLE WITH        │
│   POLAR AND NONPOLAR ANALYTES   │
│              301                │
└─────────────────────────────────┘
                 │
┌─────────────────────────────────┐
│    MIXING SAMPLE WITH SURFACTANT│
│ IN CHROMATOGRAPHICALLY WEAK SOLVENT│
│ TO FORM MICELLES WITH NONPOLAR ANALYTES│
│              302                │
└─────────────────────────────────┘
                 │
┌─────────────────────────────────┐
│  INTRODUCING MIXTURE ONTO COLUMN TO│
│    ATTAIN ON-COLUMN ENRICHMENT  │
│              303                │
└─────────────────────────────────┘
                 │
┌─────────────────────────────────┐
│  DILUTING SAMPLE TO BREAK UP MICELLES│
│              304                │
└─────────────────────────────────┘
                 │
┌─────────────────────────────────┐
│          PERFORMING A           │
│   REVERSE-PHASE GRADIENT ELUTION│
│    TO SEPARATE SAMPLE ANALYTES  │
│              305                │
└─────────────────────────────────┘
```

*Figure 3*

CHROMATOGRAPHIC METHOD WITH MICELLAR ON-COLUMN ENRICHMENT

BACKGROUND OF THE INVENTION

This is a continuation-in-part of U.S. patent application Ser. No. 07/487,332, filed Mar. 1, 1990, now abandoned.

The present invention relates to chemical analysis systems, and more particularly, to an enhanced chromatographic method for separating sample analytes having a wide range of polarities.

Analytical chemistry has advanced our understanding of living systems by breaking down complex molecules, such as proteins, into analytes that can then be separated for identification and quantitation. "Chromatography" refers to a class of techniques involving partitioning analytes between a stationary phase and a mobile phase. The analytes flow with the mobile phase, but are delayed in proportion to their partitioning to the stationary phase. The delays result in the analytes being separated in the mobile phase.

In high performance liquid chromatography (HPLC), a sample is injected onto a small-bore column packed with a stationary phase, e.g., a solvent absorbed by a supporting substance. A liquid mobile phase is then pumped through the stationary phase, ushering the sample through the column. As the sample passes through the column, each sample is partitioned between the stationary phase and the mobile phase.

Separation is achieved by selective component retention by the solid phase. Retention time for a component is related to its capacity factor k', which can be expressed as the product of the distribution coefficient and stationary phase volume divided by the interstitial mobile phase volume. Separation of different components requires that they have different capacity factors. If the capacity factors of different sample components are too small, the separation will be poor. Large capacity factors improve separations but increase band width and lengthen analysis times.

Ideally, sample components pass through the separation column in relatively discrete bands. The bands then emerge from the separation column in increasing order of their distribution coefficients. The analytes can be collected and/or detected seriatim as they elute. Components can be identified by the time of retention by the column and can be quantified by the corresponding detection peak area, which corresponds to the amount of the component responsible for the peak.

The degree to which analytes having similar capacity factors can be resolved depends in part on the length of the sample plug at the head of the column at the onset of the separation process. The length of this plug is proportional to the sample volume, which is the volume of sample in solution. The amount of solvent should be minimized to minimize sample volume, and yet be sufficient to dissolve the entire sample.

"On-column" enrichment is a technique for attaining a shorter plug for a given sample volume by using a chromatographically weak solvent, i.e., a solvent that causes analytes to have relatively large capacity factors. Due to the larger capacity factors, analytes in a chromatographically weak solvent distribute preferentially to the solid phase. The analyte molecules can be thus "held up", causing the analytes to be concentrated at the head of the column.

This on-column enrichment results in an initially narrower sample plug. The subsequent introduction of a chromatographically strong mobile phase causes the analytes to elute through the column at rates corresponding to their capacity factors. While band broadening inevitably occurs during separation, the eluting bands are narrower to the extent that enrichment narrowed the initial sample plug. The narrower analyte bands are more readily resolved. On-column enrichment thus enhances the detection and quantification of analytes, especially when small quantities are involved. See P. Schauwecker et al. in "Trace Enrichment Techniques in Reversed-Phase High-Performance Liquid Chromatography," *Journal of Chromatography* 136(1977)63–72.

If the chromatographically weak solvent used for on-column enrichment is also used as the mobile phase for separating a sample, excessive band broadening can occur. Analytes have larger capacity factors in a chromatographically weak mobile phase. Therefore, the analytes distribute more preferentially to the solid phase and progress through a column more slowly. As a result, there is more time for diffusion to effect band broadening.

Excessive band broadening can be combatted by using reverse-phase gradient elution, in which the mobile phase is gradually changed from a relatively polar (weak) solvent to a relatively nonpolar (strong) solvent. When the mobile phase is polar, nonpolar components are preferentially distributed in the stationary phase and the polar components advance through the column. As the mobile phase is gradually changed to nonpolar, the nonpolar components begin to separate and follow the polar components through the column. The method shortens the time that nonpolar compounds are retained on the column and therefore reduces diffusion. In addition to reducing analysis time, gradient elution improves peak shape and thus increases effective detection sensitivity.

Samples with a wide range of polarities (capacity factors) pose a challenge to on-column enrichment. If the solvent is too weak, it may fail to dissolve some of the more polar analytes. Alternatively, the relatively high concentration of weak solvent required to dissolve all analytes can substantially offset the advantages of on-column enrichment. On the other hand, use of a stronger solvent eliminates or diminishes the effectiveness of on-column enrichment. What is needed is a method that more effectively attains the advantages of on-column enrichment given a sample with a wide range of polarities.

SUMMARY OF THE INVENTION

In accordance with the present invention, a solution of sample, polar solvent, and surfactant is introduced onto a column. The concentration of the polar solvent is sufficient to dissolve polar analytes, but insufficient to dissolve at least some nonpolar analytes in the absence of the surfactant. The surfactant forms micelles with the nonpolar analytes, aiding in their dissolution. Once sample introduction is complete, the solution is diluted so that the micelles break up. A reverse-phase gradient elution is then used to separate the analytes. The preferred surfactant can be a polyoxyethylenated sorbitan such as polyoxyethylenated sorbitan monooleate.

In practice, the steps of the inventive method need not proceed discretely. More generally, micelles should be maintained until at least a predominant proportion of the sample is on the column head. Also, a predominant proportion of the separation has occurred. "Predominant proportion" herein means more than half. For best results, the predominant proportion in each instance should be as close to unity as possible.

A major advantage of the present invention is that it allows on-column enrichment of a sample with a wide range of polarities, such as samples containing a variety of amino acids. As a result, more concentrated analyte peaks and, thus, more sensitive detection and quantitation are provided. Empirical studies indicate that this enhanced sensitivity is attained without a comparable decrease in band separation in the eluting bands. In effect, the addition of surfactant causes the range of polarities to be compressed temporarily for the purpose of on-column enrichment in preparation for a separation during which the range of polarities is at least partially restored. The relatively narrow sample plug resulting from on-column enrichment yields greater resolution. Concomitantly, peak heights are increased, providing more reliable detections and more precise quantification of analytes. These and other features and advantages of the present invention are apparent from the description below with reference to the following drawings.

BRIEF DESCRIPTION OF THE DRAWINGS

FIG. 3 is a flow chart of the method of the present invention.

In the figures, a three-digit number referring to an element of the drawings has as its first digit the figure number in which the element is introduced in the description below. For example, chromatographic column 110 is first introduced with reference to FIG. 1 and stationary phase packing material 203 is first introduced with reference to FIG. 2. This is intended to aid the reader in locating referents.

DESCRIPTION OF THE PREFERRED EMBODIMENTS

Figure 1:
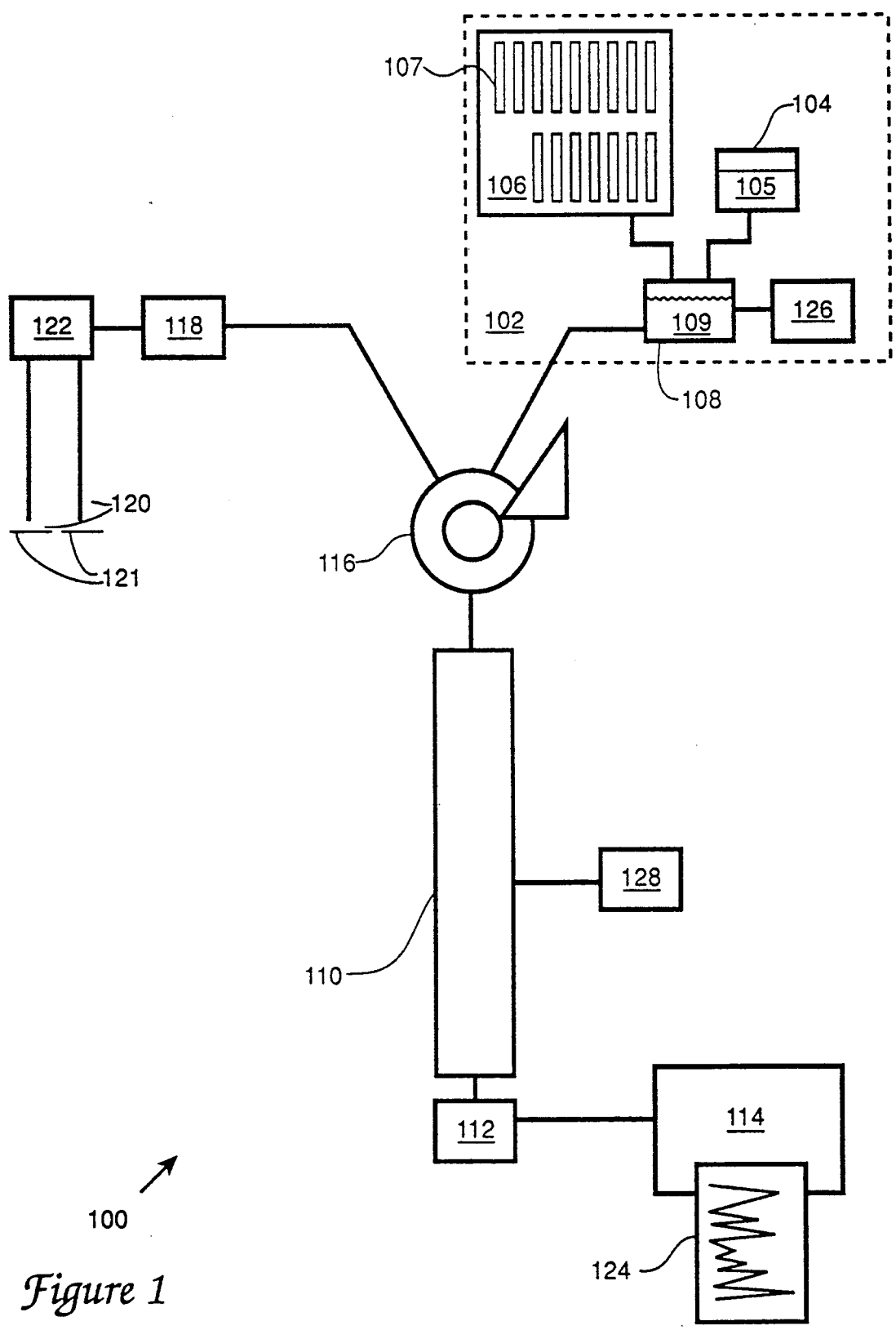
FIG. 1 is a schematic illustration of an analytical system in which the method of the present invention is practiced.

A chromatographic system 100 comprises a sample preparation device such as a protein sequencer 102, a sample manipulator 104, a sample 105 containing analytes, a source 106 of preparation solvents, cleaving solvents, and surfactants, a sample-surfactant reservoir 108, a chromatographic column 110, a detector 112, and a peak processor 114, as shown in FIG. 1. In accordance with the present invention, the sample 105 issuing from sample manipulator 104 is mixed with a surfactant solution 107 also stored in source 106, to yield a sample-surfactant mixture 109 which is stored in sample-surfactant reservoir 108. Sample-surfactant mixture 109 is then injected onto column 110 by a sample injector 116. A column pumping system 118 pumps mobile phase solvents 120, stored in mobile-phase containers 121, through column 110. The composition of the mobile phase is mediated by a gradient programmer 122. The temperatures of sample-surfactant reservoir 108 and column 110 are controlled by temperature controllers 126 and 128, respectively.

Figure 2:
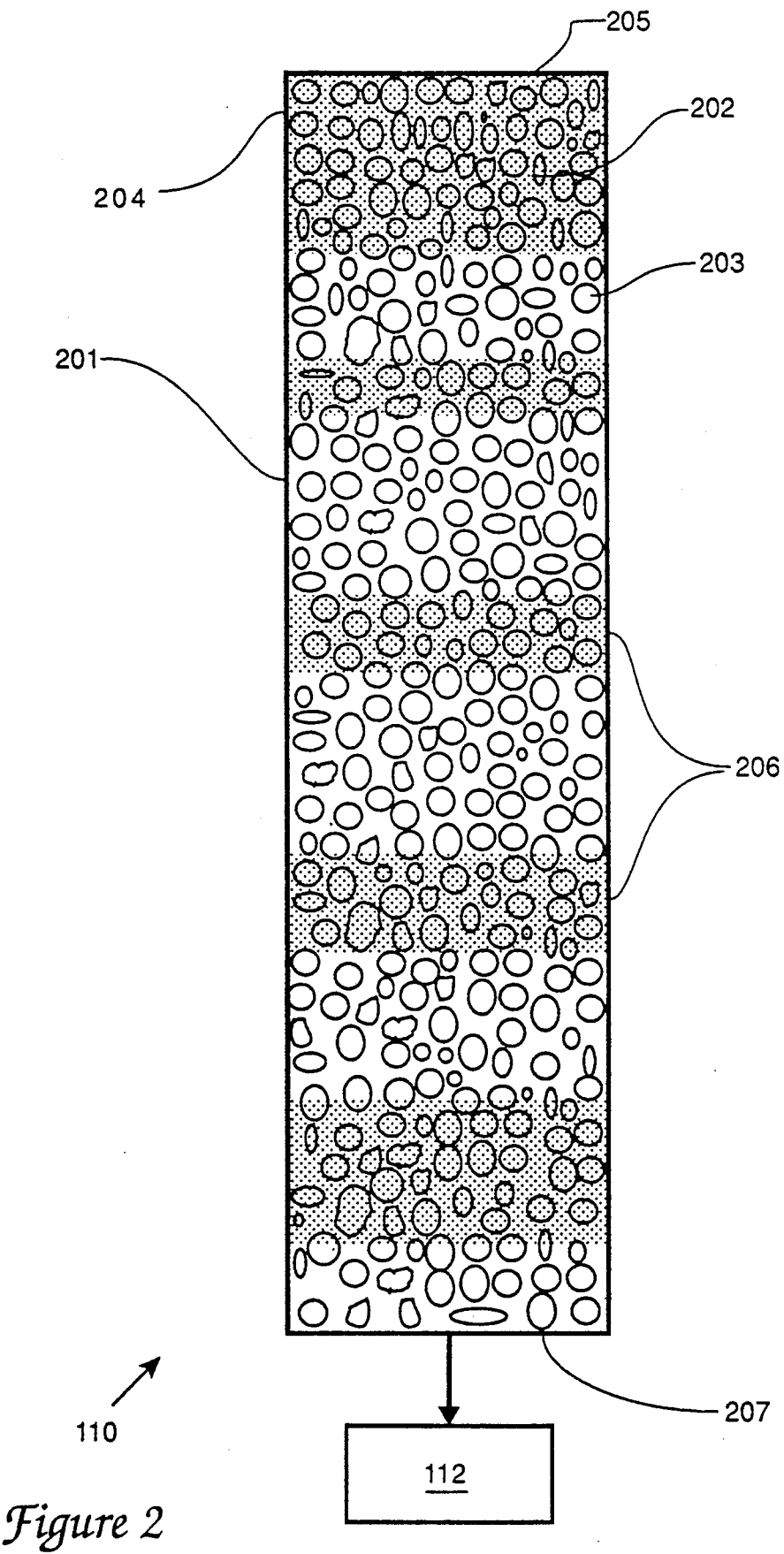
FIG. 2 is a detailed view of a portion of a chromatography column of the system of FIG. 1.

Column 110 comprises an elongated stainless steel tube 201 filled with packing 203 of octadecyl silane-modified silica spheres, as shown in FIG. 2. Packing 203 serves as the stationary phase for elution. Column 110 has a column head 204 where a sample plug 202 is formed when mixture 109 is introduced through an inlet end 205. Tube 201 has an inner diameter of about 2.1 millimeters (mm) and is 10–30 centimeters (cm) long. As the mobile phase is introduced, mixture 109 separates into component bands 206, which exit tube 201 through its outlet end 207 and progress past detector 112 for detection. Detector 112 is a UV-visible spectrophotometer which measures the absorbance and/or the absorption spectra of components. The concentrations of the respective analytes are readily calculable from the absorbances of component bands 206.

In accordance with a method 300 of the present invention, a sample is obtained, at step 301 of FIG. 3, pursuant to an Edman degradation using sequencer 102. The sample comprises a number phenylthiohydantoin amino acids having a wide range of polarities.

The sample is mixed with the water-surfactant mixture 107 at step 302. The sample is dissolved in the solution. The water alone is sufficient to dissolve the more polar analytes. However, the surfactant is required to dissolve the nonpolar analytes. Sufficient surfactant is added so that the concentration of surfactant in the sample-surfactant solution 109 exceeds the critical micelle concentration to form micelles of nonpolar analytes. Micelles are not formed with the already dissolved polar analytes. Elevated mixture temperatures can enhance enrichment by increasing micellar solubility. Therefore, temperature controller 126 is provided for heating sample-surfactant reservoir 108. Micelle formation is addressed by Rosen & Goldsmith in *Systematic Analysis of Surface-Active Agents* (Wiley, New York, 2d ed. 1972), pp. 18 ff.

The sample-surfactant solution 109 is introduced, at step 303, onto chromatographic column 110, which is packed with a nonpolar solid phase. In this context, water is a chromatographically weak solvent. Introduction of the sample-surfactant solution effects on-column enrichment.

Once sample introduction is completed, the sample is diluted, at 304, so that the micelles are broken up on column. Dilution is effected simply by pumping mobile phase without surfactant onto the column. In practice, it is possible that the mobile phase will wash additional sample onto the column. Conservatively, more than half the sample is on column before surfactant-free mobile phase is pumped onto the column. As the pumped mobile phase mixes with sample-surfactant solution, the surfactant concentration falls below the critical micelle concentration, initiating breakup of the micelles. Further introduction of mobile phase insures the breakup and washes surfactant from the column. Surfactant, including that associated with the micelles, elutes prior to the analytes and/or is not detected, thus avoiding interference with the peaks of interest.

Sample components are then separated, at step 305, during reverse-phase gradient elution. Water and 15% acetonitrile is the initial polar solvent in the reverse-phase gradient elution. There is no discrete change that separates micellar breakup and analyte migration through the column. However, the micelles are effectively gone relatively early in the separation process. During the reverse-phase gradient elution, isopropanol is introduced into the mobile phase, which thus becomes less polar and chromatographically stronger. The proportion of isopropanol in the water-isopropanol mobile phase is gradually increased to unity. The analyte peaks are detected in a conventional manner as they elute from column 110.

Sample 105 is provided by sequencer 102 which implements an Edman degradation procedure useful in peptide analysis. Edman degradation can produce picomole quantities of samples containing components with a wide range of polarities. The sample output from sequencer 102 is collected and dried.

Surfactant solution 107 is preferably a 0.1% aqueous solution of polyoxyethylenated sorbitan monooleate, manufactured under the tradename "Tween 80" by Atlas Chemical Industries, Wilmington, Del. Water used in the preparation of the aqueous solution must be purified and deionized, as, for example, by a HP661A water purifier (manufactured by Hewlett-Packard Co., USA). The water can be two times glass-distilled or quartz-distilled, avoiding contact with plastic, which causes ghost peaks. The surfactant is stored in surfactant and solvent source 106. Fifty to one hundred $\mu$L of the surfactant solution is mixed with the dried sample. Sample-surfactant mixture 109 is immediately injected onto column 110 via injector 116. Other embodiments alternatively use solutions of lower concentrations or greater concentrations so long as the injection concentration of surfactant remains above the critical micelle concentration.

Injector 116 includes a valve loop injector under sequencer control. The injector removes at least some of the mixture from sample-surfactant reservoir 108 and injects the mixture onto column 110. Once the sample is injected, injector 116 couples column pumping system 118 to column 110 so that elution can begin.

Column pumping system 118 forces one or more mobile phase solvents 120 through column 110. The mixture of one or more of the mobile phase solvents can be varied by mediation of gradient programmer 122 to decrease the polarity of the mobile phase. The gradient program can provide for gradual or stepwise gradient elution as desired. The polar and the entrained nonpolar components are then separated as they pass through column 110 to detector 112. Components are then identified by their time of elution as reflected in chromatogram 124.

The increased effectiveness of the system resulting from the present invention allows the use of a shorter column 110, or alternatively allows the separation of more complex samples. The time of analysis can be decreased, so that a sample that decomposes within hours, such as some components of the product of Edman degradation, can be injected without delay and processed rapidly.

Although in the preferred embodiment mixing occurs by diffusion in the sample-surfactant reservoir 108, other mixing methods are compatible with the invention. The mixing of the surfactant and sample can be accomplished by adding the surfactant to the sample and blending them, or by any other method of combination of sample and surfactant. In the preferred embodiment, a diluted surfactant is added to a dried sample. Alternatively, surfactant can be added to a partially dissolved sample. The sample and surfactant can be manually mixed before injection onto column 110. The samples can be injected simultaneously onto the column so that they mix during injection. The sample can be injected onto a surfactant-filled head. The surfactant can be injected onto the sample plug. In some cases, dilution will begin before all of the sample is on the column head. However, at least the predominant portion of the sample should be on-column before dilution begins.

Surfactants can include nonionic and ampholytic surfactants. In addition to polyoxyethylenated sorbitan monooleate, other nonionic surfactants are provided for, including a preparation of polyoxyethylenated sorbitan monolaurate manufactured as "Tween 20" by Atlas Chemical Industries; other esters, ethers, and glycols, including long-chain carboxylic esters of glycols, glucosides, and sorbitols; ethers of glycols, such as alkyl and alkylphenyl ethers of (poly)oxyethylene glycols; and polyoxyethylenated polyoxypropylene glycols. Mobile phase solvents can include commonly used reverse-phase solvents such as water, methanol, acetonitrile, and tetrahydrofuran, and buffers such as sodium acetate.

The present invention is applicable to a wide range of sample materials, including peptides such as proteins, protein fragments, peptide chains, and peptide fragments, and to soils and pesticide analyses, and analyses of endogenous and exogenous blood components. Other sequencers are compatible with the invention, including sequenators. Other sources for the eluted sample are also provided for.

Alternative means for sample injection may also be used, including an automatic sample injector with a syringe which is guided by robot control. Other detectors are also compatible with the invention. If a fused-silica tube is used, quantitative concentration measurements can be taken without disturbing equilibria under consideration, and thus can be used to detect eluate bands 206 while they are still on column 110. These and other variations upon and modifications to the described embodiments are provided for by the present invention, the scope of which is limited only by the following claims.

What is claimed is:

1. A method for separating the component analytes of a sample, said analytes having a range of polarities in a chromatographic column, said sample having at least one relatively polar analyte and at least one relatively nonpolar analyte, said method comprising the steps of:

mixing a surfactant with said sample in a relatively chromatographically weak solvent so as to form a solution containing micelles of said nonpolar analyte, the concentration in said solution of said chromatographically weak solvent being sufficient to dissolve said polar analyte but being insufficient to dissolve said nonpolar analyte in the absence of said surfactant;

introducing said solution containing said micelles and said polar analyte onto the head of said chromatographic column, the concentration of surfactant being maintained at a sufficient level to maintain said micelles at least until a predominant portion of said sample is on the head of said column;

diluting said sample so that said micelles break up; and separating said analytes by reverse phase gradient elution through said column, said reverse phase gradient elution proceeding from said relatively chromatographically weak solvent to a relatively chromatographically strong solvent, said reverse phase gradient elution being times so that separation of said analytes occurs predominantly after a predominant proportion of said micelles break up.

2. The method of claim 1 wherein said surfactant includes a polyoxyethylenated sorbitan.

3. The method of claim 1 wherein said surfactant includes polyoxyethylenated sorbitan monooleate.

4. A method for separating amino acids in a sample, said amino acids having a range of polarities in a chromatographic column, said sample having at least one relatively polar amino acid and at least one relatively nonpolar amino acid, said method comprising the steps of:

mixing a surfactant with said sample in a relatively chromatographically weak solvent so as to form a solution containing micelles of said nonpolar amino acid, the concentration in said solution of said chromatographically weak solvent being sufficient to dissolve said polar amino acid but being insufficient to dissolve said nonpolar amino acid in the absence of said surfactant;

introducing said solution containing said micelles and said polar amino acid onto the head of said chromatographic column, the concentration of surfactant being maintained at a sufficient level to maintain said micelles at least until a predominant portion of said sample is on the head of said column;

diluting said sample so that said micelles break up; and separating said amino acids by reverse phase gradient elution through said column, said reverse phase gradient elution proceeding from said relatively chromatographically weak solvent to a relatively chromatographically strong solvent, said reverse phase gradient elution being timed so that separation of said analytes occurs predominantly after a predominant proportion of said micelles break up.

* * * * *